United States Patent [19]
Haber et al.

[11] Patent Number: 5,269,766
[45] Date of Patent: Dec. 14, 1993

[54] DENTAL SYRINGE HAVING AN AUTOMATICALLY RETRACTABLE MEDICATION CARPULE AND NEEDLE CANNULA

[75] Inventors: Terry M. Haber, El Toro; William H. Smedley, Lake Elsinore; Clark B. Foster, Laguna Niguel, all of Calif.

[73] Assignee: Habley Medical Technology Corporation, Laguna Hills, Calif.

[21] Appl. No.: 895,892

[22] Filed: Jun. 9, 1992

[51] Int. Cl.$^5$ ............................................. A61M 5/32
[52] U.S. Cl. .................................... 604/198; 604/232
[58] Field of Search ............... 604/192, 197, 198, 194, 604/110, 232-235, 187, 135

[56] References Cited

U.S. PATENT DOCUMENTS

| | | |
|---|---|---|
| 2,876,770 | 3/1959 | White . |
| 3,780,734 | 12/1973 | Walff .................. 604/197 |
| 4,573,976 | 3/1986 | Sampson et al. . |
| 4,592,745 | 6/1986 | Rex et al. ............. 604/232 |
| 4,664,654 | 5/1987 | Strauss . |
| 4,767,413 | 8/1988 | Haber et al. ......... 604/232 |
| 4,772,272 | 9/1988 | McFarland . |
| 4,795,443 | 1/1989 | Permenter et al. . |
| 4,801,295 | 1/1989 | Spencer . |
| 4,834,717 | 8/1989 | Haber et al. ......... 604/232 |
| 4,932,947 | 6/1990 | Cordwell ............. 604/198 |
| 4,957,490 | 9/1990 | Byrne et al. ......... 604/110 |
| 4,994,042 | 2/1991 | Vadher ................ 604/198 |
| 5,013,301 | 5/1991 | Marotta, Jr. et al. .. 604/198 |
| 5,088,988 | 2/1992 | Talohn et al. ........ 604/232 |
| 5,106,379 | 4/1992 | Leap .................... 604/198 |

FOREIGN PATENT DOCUMENTS 642987 6/1962 Canada .
2202747 10/1988 United Kingdom .

Primary Examiner—C. Fred Rosenbaum
Assistant Examiner—Chalin Smith
Attorney, Agent, or Firm—Hawes & Fischer

[57] ABSTRACT

A reusable dental syringe having a hollow cylinder, a prefilled medication carpule to be received within the cylinder, and a hypodermic needle cannula communicating with the carpule and extending outwardly from the cylinder for administering an injection. The syringe also includes a retaining collar which can be moved, against the normal bias of a compression spring, axially and distally through the cylinder and into engagement with the carpule. A slide lock is adapted to lock the retaining collar at the distal position within the cylinder. After a injection has been administered and the carpule emptied, the slide lock may be moved to release the retaining collar from the distal position. The compression spring is now free to return to its normal bias, whereby to drive the retaining collar and the empty carpule connected thereto axially and proximally through the cylinder. Accordingly, the needle cannula is automatically relocated from the outwardly extended position to a retracted position within the cylinder so as to prevent an accidental needle stick and the spread of a contageous, and possibly life threatening, disease.

20 Claims, 1 Drawing Sheet

DENTAL SYRINGE HAVING AN AUTOMATICALLY RETRACTABLE MEDICATION CARPULE AND NEEDLE CANNULA

BACKGROUND OF THE INVENTION

1. Field of the Invention

This invention relates to a reusable dental syringe having a combination medication carpule and needle cannula and to a slide lock that is movable to either lock the needle cannula at an outwardly extending position relative to the cylinder, at which an injection may be administered, or to release the needle cannula to be automatically retracted within and surrounded by the cylinder, so as to avoid an accidental needle stick and the possible spread of disease.

2. Prior Art

Syringes of the type having a prefilled carpule of fluid medication and a hypodermic needle cannula are well known in the art for injecting such medication from the carpule to a targeted tissue area of a patient. At the conclusion of the injection, the needle cannula typically remains locked in an axially extended position projecting outwardly from the syringe cylinder. In some cases, the syringe may be used to treat a patient having a communicable disease. Medical workers are especially susceptable to accidental and potentially infectious needle sticks due to the careless handling and disposing of the syringe after use. The resulting mini-accident caused by an accidental needle stick typically requires a blood test for such diseases as AIDS and hepatitis. The corresponding cost and inefficiency of testing medical workers who have received such an accidental needle stick result in considerable waste, which may be particularly damaging to a medical facility which is striving for economy.

The following patent, which has been assigned to the assignee of the present patent application, discloses a reusable dental syringe including a prefilled medication carpule and means for retracting a needle cannula after an injection has been administered: U.S. Pat. No. 4,931,040 issued Jun. 5, 1990.

SUMMARY OF THE INVENTION

In general terms, a reusable dental syringe is disclosed including a hollow cylinder having open proximal and distal ends, a prefilled medication carpule to be received within the cylinder, and a hypodermic needle cannula communicating with the carpule and extending outwardly from the distal end of the cylinder for administering an injection. A hollow retaining collar is connected to a radially extending handle. The collar extends from the handle into the open proximal end of the cylinder around which is formed a radially extending flange. A helical compression spring surrounds the retaining collar between the handle and flange. A locking tooth projects outwardly from the retaining collar. A slide lock is received in and slidable laterally through a slot formed in the flange. The slide lock has a central opening through which the retaining collar may be reciprocated. The slide lock has at least one catch formed therein for selectively engaging the locking tooth of the retaining collar.

In operation, the handle of the syringe is moved towards the flange, whereby to compress the spring therebetween and advance the retaining collar axially and distally through the central opening of the slide lock and into the cylinder, whereby to engage one end of the carpule. The catch of the slide lock engages the locking tooth of the retaining collar to retain the collar at the distally advanced position and lock the needle cannula in the outwardly extending position relative to the cylinder. A detachable piston stem is then depressed for driving an associated piston through the carpule for injecting the medication from the carpule into the targeted tissue area of a patient via the cannula.

At the conclusion of the injection, the slide lock is moved through its slot, whereby to correspondingly move the catch of the slide lock out of engagement with the locking tooth of the retaining collar. The spring is now free to return to its relaxed condition, whereby the stored potential energy thereof drives the syringe handle away from the syringe flange. Likewise, the retaining collar, which is connected to said handle, is driven axially and proximally through the central opening of the slide lock. The proximal travel of the retaining collar is transferred to the carpule for moving the carpule proximally through the cylinder. Accordingly, the needle cannula is automatically relocated from the axially extended position at which the injection was administered to a retracted position at which to be surrounded and shielded within the cylinder, whereby to reduce the possibility of an accidental needle stick and the spread of a contagious, and possibly life threatening, disease.

The slide lock may be moved out of engagement with the retaining collar to permit the proximal relocation of the retainning collar and the automatic retraction of the cannula into the cylinder by laying either side of the syringe on a flat surface (e.g. an instrument tray, a table, or the like) so that the lock is contacted and moved laterally through its slot by said flat surface. The combination carpule/cannula may then be ejected from the cylinder and discarded.

DESCRIPTION OF THE PREFERRED EMBODIMENT

Figure 1:
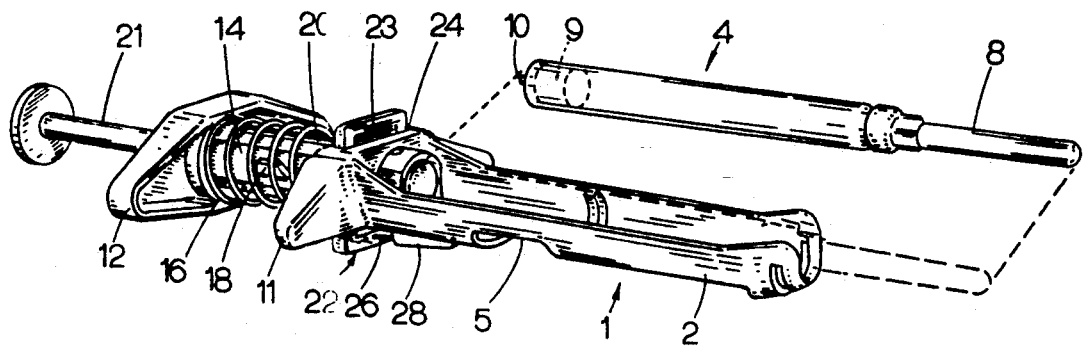
FIG. 1 is an isometric drawing of the reusable dental syringe which forms the present invention and a combination medication carpule and needle cannula which is to be used therewithin.

The reusable dental syringe which forms the present invention and the retractable medication carpule and needle cannula thereof are best described while referring to the drawings where such a dental syringe 1 is illustrated. The presently disclosed dental syringe 1 preferably includes certain elements that are common to a commercially available syringe. Such a commercially available dental syringe is sold under the name CARPUJECT by Winthrop-Breon Corporation of New York. However, it is to be expressly understood that the teachings of this invention are not limited to the above-mentioned syringe and other syringe configurations could be employed in combination with the present invention to achieve the advantages offered thereby.

Figure 2:
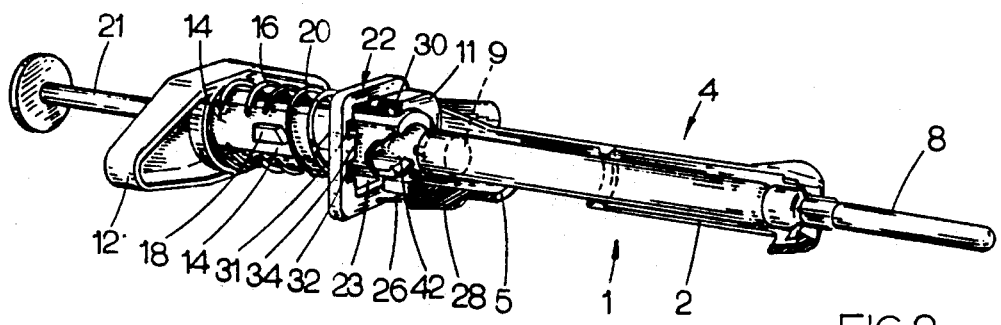
FIG. 2 shows the combination carpule and cannula as received within the cylinder of the dental syringe of FIG. 1.

Referring initially to FIGS. 1 and 2 of the drawings, the preferred dental syringe 1 is shown including a hollow, elongated cylinder 2 having open proximal and distal ends. A prefilled medication carpule 4 is removably snap fit within the hollow interior of cylinder 2 (best illustrated in FIG. 2). The front face of the cylinder 2 is removed so that a health care worker will have visible access to the entire carpule 4 being carried therewithin. A window 5 is removed from the opposite face of cylinder 2 to aid the health care worker in ejecting an empty carpule therefrom after an injection has been administered. Carpule 4 is a disposable, medication filled cartridge of the type that is available from the above-named manufacturer, as well as from other sources. Carpule 4 has an associated hypodermic needle cannula (designated 6 in FIGS. 3 and 4) and a removable needle shield 8 which preserves the sterility of of the cannula while preventing an accidental needle stick prior to the administration of the injection.

Carpule 4 also has an associated piston 9 which is adapted for axial movement therethrough to expulse the medication from the carpule during the administration of an injection. A screw threaded fitting 10 projects outwardly from piston 9 for connection to a piston stem so as to complete a piston assembly.

The proximal end of the syringe cylinder 2 terminates at an integral, radially projecting flange 11 under which the fingers of a health care worker are placed during the administration of an injection. Spaced above and arranged in parallel alignment with the flange 11 is a radially projecting handle 12 having a hollow retaining collar 14 integrally formed with and extending therefrom. The inside diameter of retaining collar 14 is slightly larger than the outside diameter of carpule 4, so that one end of the carpule may be received within and retained by collar 14. A helical compression spring 16 surrounds retaining collar 14 between the flange 11 and the handle 12. A locking tooth 18 having an inclined end projects outwardly from one of the sides of retaining collar 14. The side of retaining collar 14 from which locking tooth 18 projects and the opposite side thereof are formed as flat, planar surfaces (best depicted in FIG. 2). A longitudinally extending guide slot 20 runs along the top of retaining collar 14. The purposes of and advantageous effects provided by the compression spring 16, locking tooth 18, and guide slot 20 will be described in greater detail hereinafter.

An elongated piston stem 21 is received through a hole in handle 12 and the hollow interior of retaining collar 14 to be detachably connected to the piston 9 of carpule 4. The piston stem 21 has a screw threaded receptacle (not shown) which is adapted to be rotated into engagement with the screw threaded fitting 10 of piston 9 at the interior of syringe cylinder 2, whereby to complete a piston assembly for selectively controlling the axial movement of piston 9 through carpule 4 during the administration of an injection.

Syringe 1 is provided with a slide lock 22 by which to automatically lock (and subsequently release) the medication carpule 4 at a distally advanced position within cylinder 2 so that the needle cannula 4 is retained at an outwardly extended position relative to cylinder 2 for the purpose of penetrating the skin of a patient so that an injection can be efficiently administered. More particularly, the slide lock 22 is shown as a generally rectangular member having a central opening 23 (best illustrated in FIG. 2) surrounded by an outer frame. Slide lock 22 is sized to be received within a correspondingly sized slot 24 which extends transversely through flange 11. To this end, a centering spring 26 is connected between the slide lock 22 and a tab 28 which is affixed (e.g. at the bottom) of syringe cylinder 2. Centering spring 26, which may be a straight piece of wire, or the like, performs the multiple functions of preventing the removal of slide lock 22 from its slot 24, permitting the slide lock 22 to slide laterally a controlled distance through slot 24, and automatically centering the central opening 23 of slide lock 22 so that the locking and releasing of the carpule 4 may be reliably achieved in a manner which will soon be disclosed.

The central opening 23 of slide lock 22 is sized to accommodate the retaining collar 14 therethrough (also best illustrated in FIG. 2). As will soon be described, the retaining collar 14 is adapted for reciprocal movement through central opening 23 to control the relocation of medication carpule 4 and its associated cannula 6 relative to syringe cylinder 2. A guide pin 30 (best shown in FIG. 2) extends downwardly from handle 11 for receipt in the longitudinal guide channel 20 at the top of retaining collar 14. Guide pin 30 rides through guide channel 20 during the reciprocal movement of the retaining collar 14 through the central opening 23 of slide lock 22 for the purpose of limiting the proximal travel of retaining collar 14 and, thereby, preventing the inadvertent removal of collar 14 from the cylinder 2 through the open proximal end thereof. That is to say, the axial distance travelled by retaining collar 14 in a proximal direction through cylinder 2 at the conclusion of an injection (which travel will be imparted to carpule 4 and cannula 6) is dependent upon the length of guide channel 20 through which the guide pin 30 will ride.

As is best shown in FIG. 2, a pair of detents 31 and 32 are located adjacent one another on the same side of the outer frame of slide lock 22. A catch 34 is formed between detents 31 and 32. As will be described in greater detail when referring to FIGS. 3 and 4, the detents 31 and 32 and catch 34 of slide lock 22 cooperate with the locking tooth 18 of retaining collar 14 when such collar 14 moves distally through the central opening 23 of slide lock 22 to automatically lock (and subsequently release) the medication carpule 4 an its associated needle cannula 6 at an outwardly extended position relative to syringe cylinder 2 so that an injection may be administered.

Figure 3:
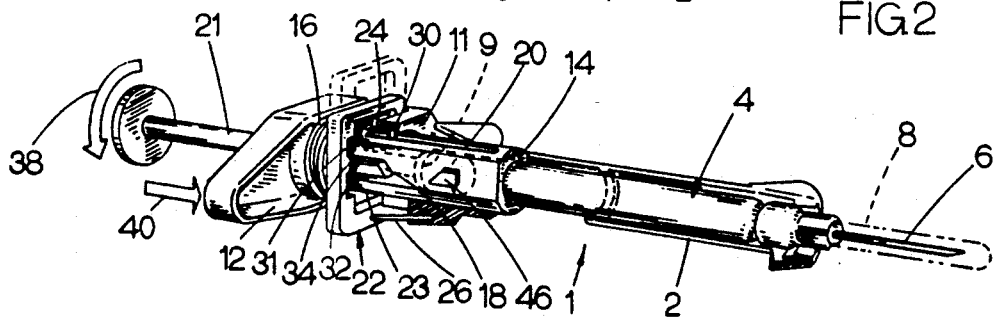
FIG. 3 illustrates the steps by which the medication carpule is engaged by a hollow retaining collar at the interior of the syringe cylinder.
Figure 4:
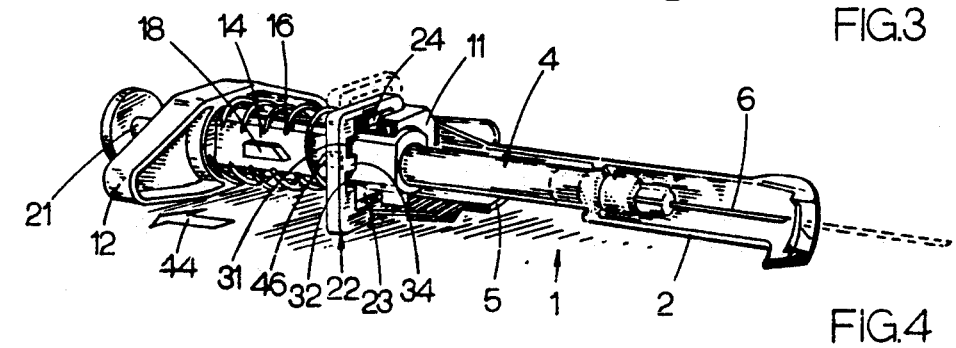
FIG. 4 illustrates the steps by which the combination carpule and cannula may be automatically retracted within the syringe cylinder after an injection has been administered.

The operation of the dental syringe 1 of the present invention is now described while referring to FIGS. 2–4 of the drawings. In FIG. 2, the combination medication carpule 4 and needle cannula 6 is shown removed from its shipping container and snapped into engagement with the interior of the syringe cylinder 2 such that needle cannula 6 extends outwardly through the open distal end thereof. The cannula 6 is initially surrounded and protected by the needle shield 8. The carpule 4 is loaded into cylinder 2 so as to be spaced axially and distally from the hollow retaining collar 14. Therefore, the locking tooth 18 of collar 14 is spaced proximally from slide lock 22 and compression spring 16 is relaxed. Moreover, the piston stem 21 is detached from the piston 9 of carpule 4.

In FIG. 3, the piston stem 21 is shown after it is rotated (in the direction of reference arrow 38) through the hollow retaining collar 14 and into contact with the threaded end of piston 9 so as to complete a piston assembly for driving the piston through the medication carpule 4 and expulsing the medication therefrom via cannula 6. The health care worker may locate his index and middle fingers below the flange 11 and his thumb upon handle 12 so as to apply an axial and distally directed force (in the direction of reference arrow 40) for moving handle 12 towards flange 11. Thus, the coil spring 16 is compressed between flange 11 and handle 12. The integral retaining collar 14 of handle 12 is correspondingly moved axially through the central opening 23 of slide lock 22 and into syringe cylinder 2 (via the open proximal end thereof), whereby the guide pin 30 rides through longitudinal guide channel 20 and an end of carpule 4 is received within and retained (by means of a friction fit) at the hollow interior of collar 14. Such friction fit between retaining collar 14 and carpule 4 may be enhanced by an integral, spring-like tongue 42 which extends inwardly of collar 14 for engaging the carpule.

By virtue of the present invention, the carpule 6 is automatically locked in the outwardly extending position relative to the open distal end of cylinder 2, so as to permit the health care worker to relocate his thumb from the handle 12 to the piston stem 21 for controlling the movement of piston 9 through carpule 4. More particularly, the axial movement of retaining collar 14 through slide lock 22 correspondingly moves the locking tooth 18 of collar 14 into contact with the catch 34 which is located between the detents 31 and 32 of lock 22. The continued axial movement of retaining collar 14 into cylinder 2 and towards carpule 4 causes catch 34 to ride up the inclined end and over the top of locking tooth 18, whereby to also cause lock 22 to slide laterally (as shown in phantom) through its transverse slot 24 in flange 11 and thereby stress the centering spring 26. The lateral movement of slide lock 22 through slot 24 aligns said lock so that locking tooth 18 can pass through the detent 32 formed therein. When retaining collar 14 is moved through the cylinder 2 and into engagement with an end of carpule 4, the locking tooth 18 will have travelled across and dropped behind the catch 34. The energy stored within centering spring 26 will return slide lock 22 to its original position in slot 24 as spring 26 returns to its pre-stressed configuration. With the catch 34 of slide lock 22 located behind the locking tooth 18 of retaining collar 14, the proximal travel of collar 14 (and the carpule 4 connected thereto) through cylinder and lock 22 is blocked. Therefore, the needle cannula 6 is locked in the outwardly extending position relative to cylinder 2 so that an injection may be administered.

At this time, the health care worker removes the needle shield 8 to expose the cannula 6 for penetrating the targeted tissue area of the patient. The health care worker may then use his thumb to apply an axial and distally directed force to the piston stem 21 for driving the piston 9 through the carpule 4 and thereby expulsing the medication therefrom via cannula 6.

Referring to FIG. 4, the combination medication carpule 4 and cannula 6 is shown safely and completely retracted within the interior of the cylinder 2 of dental syringe 1 after the medication has been expulsed from the carpule. The foregoing may be advantageously and automatically accomplished whenever the syringe 1 is laid on a flat surface (e.g. an instrument tray, a table, or the like), so that slide lock 22 is moved into contact with and displaced by such flat surface. More particularly, the engagement of slide lock 22 by a flat surface will cause the lock to slide laterally (as indicated in phantom) through its slot 24 in flange 11. Accordingly, the slide lock 22 is relocated in slot 24 so that one of the detents 31 or 32 formed in the outer frame thereof will be moved into alignment with the locking tooth 18 of retaining collar 14 to permit tooth 18 to pass therethrough. The potential energy stored within the helical spring 16 (which was previously compressed between flange 11 and handle 12 during the movement of retaining collar 14 through cylinder 2 and into receipt of carpule 4) automatically drives the retaining collar 14 axially and proximally through the cylinder 2 and the central opening 23 of slide lock 22 (in the direction of reference arrow 44), such that spring 16 returns to its relaxed, pre-compressed condition and handle 12 returns to its axially spaced location relative to flange 11. Inasmuch as retaining collar 14 is connected to the carpule 4, the proximal movement of collar 14 is also transferred to carpule 4, whereby to cause the needle cannula 6 to be retracted proximally within and surrounded by the syringe cylinder 2.

By forming slide lock 22 with a pair of detents 31 and 32, either side of the syringe 1 may be placed in contact with a flat surface. That is, lock 22 is adapted to slide laterally and in opposite directions through its slot 24. The locking tooth 18 will then be aligned with one or the other of the detents 31 or 32 depending upon the end of the slide lock 22 that is moved into contact with the flat surface and the corresponding direction in which said lock slides. The ability of slide lock 22 to slide in opposite directions permits the needle cannula 6 to be released from its outwardly extended position after use and retracted into the cylinder 2 without requiring any special action on the part of the health care worker, other than to position syringe 1 such that either end of slide lock 22 is moved into contact with a flat surface. Of course, the health care worker can also activate slide lock 22 with his thumb, rather than by contact with a flat surface.

The automatic relocation of cannula 6 from the outwardly extended position relative to cylinder 2 reduces the likelihood of an accidental needle stick and the spread of the contageous, and possibly life threatening, disease. The combination carpule 4 and cannula 6 may be removed from the cylinder 2 and discarded after the piston stem 21 is rotated out of engagement with the piston of an empty carpule 4. The health care worker may use the open window 5 through cylinder 2 to assist him in ejecting the carpule/cannula combination for disposal.

It will be apparent that while a preferred embodiment of the invention has been shown and described, various modifications and changes may h=made without departing from the true spirit and scope of the invention. By way of example, a second locking tooth or lock-out 46 may project outwardly from the retaining collar 14 in spaced, axial alignment with the first tooth 18 thereof. Like the first tooth, the second tooth 46 has one inclined end. As the retaining collar 14 is driven proximally through cylinder 2 and past the central opening 23 of slide lock 22 to automatically retract needle cannula 6, the catch 34 of slide lock 22 will ride up the inclined end, travel across the top, and drop behind tooth 46. With the catch 34 located behind the locking tooth 46 (best shown in FIG. 4), the distal relocation of collar 14, and the carpule 4 which is connected thereto, is blocked. Therefore, the needle cannula 6 cannot be inadvertently returned to extend outwardly from the distal end of cylinder 2 (as shown in FIG. 3) for subjecting a health care worker to an accidental needle stick.

Having thus set forth a preferred embodiment of the invention, what is claimed is:

1. A syringe comprising:
   a cylinder having proximal and distal ends;
   a syringe body including said cylinder and having a slot extending therethrough;
   a medication filled cartridge received within and movable through said cylinder;
   a needle cannula communicating with said cartridge and extending outwardly from the distal end of said cylinder for administering an injection;
   collar means to surround and engage said medication cartridge so as to be movable therewith through said cylinder; and
   locking means movable between locked and unlocked positions, said locking means located in the locked position to engage said collar means to thereby block the relocation of said cartridge proximally through said cylinder and retain said cannula at said outwardly extending position, or said locking means moved to the unlocked position to release said collar means and thereby permit the relocation of said cartridge proximally through said cylinder and the retraction of said cannula into said cylinder, said locking means extending completely around the periphery of said collar means and having a central opening, said collar means being moved distally through said central opening for engaging the medication cartridge and proximally through said central opening for relocating the cartridge through the cylinder and thereby retracting the cannula into the cylinder;
   said locking means being slidable laterally relative to said cylinder and through said slot in said syringe body between the locked and unlocked positions in a direction which is transversely aligned with respect to the direction in which said collar means moves through the central opening of said locking means.

2. The syringe recited in claim 1, further comprising spring means for driving said collar means proximally through said cylinder to thereby relocate said cartridge and automatically retract said cannula when said locking means is located in the unlocked position.

3. The syringe recited in claim 2, wherein said spring means is a compressible spring being held in a state of compression when said locking means is in the locked position, said spring expanding when said locking means is moved to the unlocked position, the energy released by said expanding spring being transferred to said collar means to drive said collar means proximally through said cylinder and thereby relocate said cartridge connected thereto.

4. The syringe recited in claim 3, wherein said spring is a coil spring that surrounds said collar means.

5. The syringe recited in claim 1, wherein said locking means has a catch formed thereon and said collar means has a tooth projecting therefrom, said tooth being engaged by said catch when said locking means is in the locked position to block the relocation of said cartridge proximally through said cylinder, or said tooth being disengaged from said catch when said locking means is moved to the unlocked position to permit the proximal relocation of said cartridge and the retraction of said cannula.

6. The syringe recited in claim 5, wherein said locking means has an opening located at each side of said catch, the tooth of said collar means being disengaged from said catch and aligned for passage through one of said openings when said locking means is moved to the unlocked position.

7. The syringe recited in claim 1, further comprising resilient spring means connected to said locking means to prevent the removal of said locking means from said slot and to bias said locking means for movement to the locked position.

8. A syringe comprising:
   a cylinder having proximal and distal ends;
   a medication filled cartridge received within and movable through said cylinder;
   a needle cannula communicating with said cartridge and extending outwardly from the distal end of said cylinder for administering an injection;
   compression spring means biased to relocate said cartridge in a proximal direction through said cylinder to thereby automatically retract said cannula into said cylinder;
   locking means having an opening into which said cartridge is moved when said cartridge is relocated proximally through said cylinder, said locking means being located in a locked position to block the proximal relocation of said cartridge through said cylinder and into said opening whereby to retain said cannula at said outwardly extending position, or said locking means being located in an unlocked position to permit the proximal relocation of said cartridge through said cylinder and into said opening whereby to retract said cannula into said cylinder; and
   retaining means surrounded by said compression spring means and connected to said cartridge within said cylinder so that said retaining means is movable with said cartridge when said cartridge is located proximally through said cylinder, said spring means being retained in a state of compression and said retaining means being engaged by said locking means when said locking means is in the locked position to block the proximal relocation of said cartridge through said cylinder, or said retaining means being released by said locking means and said spring means expanding when said locking means is in the locked position for causing said retaining means to be driven proximally through said cylinder and said cartridge to be relocated into the opening of said locking means for retracting said needle cannula into the cylinder.

9. The syringe recited in claim 8, wherein said locking means has a catch and said retaining means has at least one tooth projecting therefrom, said tooth being engaged by said catch when said locking means is located in the locked position to prevent the proximal movement of said retaining means and the relocation of said cartridge into the opening of said locking means, and said tooth being released b said catch when said locking means is located in the unlocked position to permit the proximal movement of said retaining means and the relocation of said cartridge into said opening.

10. The syringe recited in claim 9, wherein said retaining means has a second tooth projecting therefrom, said second tooth being engaged by the catch of said locking means after said retaining means has moved proximally through said cylinder and said cartridge has moved into the opening of said locking means, the engagement of said second tooth by said catch preventing the distal movement of said cartridge through said cylinder and a return of said cannula to the outwardly extending position from said cylinder.

11. The syringe recited in claim 9, wherein said locking means has an aperture located at each side of said catch, the tooth of said retaining means being disengaged from said catch and aligned for passage through one of said apertures when said locking means is moved to the unlocked positions.

12. The syringe recited in claim 8, further comprising a syringe body including said cylinder and having a slot extending therethrough for receiving said locking means said locking means being slidable through said slot between the locked and unlocked positions in a direction which is transversely aligned with respect to the direction in which said cartridge is relocated through said cylinder.

13. The syringe recited in claim 12, further comprising resilient spring means connected to said locking means to prevent the removal of said locking means from said slot and to bias said locking means for movement to the locked position.

14. The syringe recited in claim 8, wherein said locking means is a rectangle that extends completely around the periphery of said cartridge and is slidable relative to said cartridge between the locked and unlocked positions through a plane which is perpendicularly aligned with respect to the direction in which said cartridge moves into the opening of said locking means.

15. The syringe recited in claim 8, wherein said retaining means includes a hollow sleeve that is sized to receive and engage at least one end of said cartridge by which said retaining means is connected to said cartridge.

16. The syringe recited in claim 15, further comprising a handle adapted for reciprocal movement relative to said cylinder when said spring means is compressed and relaxed, said retaining means sleeve connected to said handle and movable therewith, said spring means surrounding said sleeve between said locking means and said handle.

17. A syringe comprising:
a cylinder having proximal and distal ends;
a medication filled cartridge received within and movable through said cylinder;
a needle cannula communicating with said cartridge and extending outwardly from the distal end of said cylinder for administering an injection;
collar means to be connected to and movable with said medication cartridge through said cylinder, said collar means having first and second axially spaced teeth projecting therefrom;
means for relocating said cartridge from a distal location within said cylinder at which said cannula extends outwardly therefrom to a relatively proximal location within said cylinder at which said cannula is retracted therewithin; and
locking means movable between locked and unlocked positions, said locking means located at the locked position to engage the first tooth of said collar means to block the relocation of said cartridge away from said distal location and thereby prevent the retraction of said cannula, said locking means located at the unlocked position to be disengaged from said tooth to permit the relocation of said cartridge to said relatively proximal location and thereby retract said cannula, or said locking means located at the locked position to engage the second tooth of said collar means to block the relation of said cartridge from said relatively proximal position to said distal position and thereby prevent the return of said cannula to extend outwardly from said cylinder.

18. The syringe recited in claim 1, said syringe body further including flange means projecting radially from opposite sides thereof for receipt of a user's fingers during the administration of an injection, said slot formed through said flange means to slidably receive said locking means therein.

19. The syringe recited in claim 1, wherein said locking means is a rectangle having said central opening through which said collar means is moved.

20. The syringe recited in claim 17, further comprising a syringe body including said cylinder and having a slot extending therethrough, said locking means received in and slidable through said slot in said syringe body between said locked and unlocked positions.

* * * * *